US012604147B2

(12) United States Patent
Georganti et al.

(10) Patent No.: US 12,604,147 B2
(45) Date of Patent: Apr. 14, 2026

(54) OPERATING A HEARING DEVICE TO ASSIST THE USER IN ENGAGING IN A HEALTHY LIVING STYLE

(71) Applicant: SONOVA AG, Staefa (CH)

(72) Inventors: Eleftheria Georganti, Zürich (CH); Manuela Feilner, Egg (CH); Ulrike Lemke, Zürich (CH); Melissa Lawrence, Glarus (CH); Thomas Wessel, Männedorf (CH)

(73) Assignee: Sonova AG, Staefa (CH)

( * ) Notice: Subject to any disclaimer, the term of this patent is extended or adjusted under 35 U.S.C. 154(b) by 245 days.

(21) Appl. No.: 18/521,633

(22) Filed: Nov. 28, 2023

(65) Prior Publication Data

US 2024/0196138 A1      Jun. 13, 2024

(30) Foreign Application Priority Data

Dec. 12, 2022      (EP) ..................................... 22212819

(51) Int. Cl.
| | |
|---|---|
| *H04R 25/00* | (2006.01) |
| *A61B 5/16* | (2006.01) |
| *H04R 1/10* | (2006.01) |

(52) U.S. Cl.
CPC ........... *H04R 25/505* (2013.01); *A61B 5/165* (2013.01); *H04R 1/1083* (2013.01); *H04R 2225/41* (2013.01); *H04R 2225/43* (2013.01); *H04R 2430/01* (2013.01)

(58) Field of Classification Search
CPC  H04R 25/505; H04R 1/1083; H04R 2225/41; H04R 2225/43; H04R 2430/01
See application file for complete search history.

(56) References Cited

U.S. PATENT DOCUMENTS

| | | | |
|---|---|---|---|
| 6,023,517 A | 2/2000 | Ishige | |
| 10,362,385 B1 | 7/2019 | Di et al. | |
| 2014/0309549 A1* | 10/2014 | Selig ...................... | A61B 5/123 |
| | | | 600/559 |

(Continued)

FOREIGN PATENT DOCUMENTS

| | | | |
|---|---|---|---|
| WO | 2020015233 A1 | 1/2020 |
| WO | 2020015234 A1 | 1/2020 |
| WO | 2020261148 A1 | 12/2020 |

OTHER PUBLICATIONS

Extended European Search Report sent in application 22212819.1, mailed on May 15, 2023.

(Continued)

*Primary Examiner* — Suhan Ni
(74) *Attorney, Agent, or Firm* — ALG Intellectual Property, LLC

(57) ABSTRACT

The disclosure relates to a method of operating a hearing device configured to be worn at an ear of a user. The method comprises receiving input audio signal indicative of a sound detected in the environment; processing the input audio signal; and outputting, by an output transducer included in the hearing device, an output audio signal based on the input audio signal so as to stimulate the user's hearing. The disclosure also relates to a hearing device for operating the method, and a computer-readable medium storing instructions for performing the method.

14 Claims, 3 Drawing Sheets

(56)                    References Cited

U.S. PATENT DOCUMENTS

| | | | |
|---|---|---|---|
| 2015/0181357 A1* | 6/2015 | Krystek ............... | H04R 25/505 |
| | | | 381/315 |
| 2018/0085581 A1* | 3/2018 | Fung ................... | H04R 25/505 |
| 2021/0225365 A1 | 7/2021 | Sinha et al. | |
| 2022/0076663 A1* | 3/2022 | Carter .................... | G10L 15/08 |

OTHER PUBLICATIONS

Gannouni S. et al., Sci Rep 11, 7071 (2021). https://doi.org/10.1038/s41598-021-86345-5.

* cited by examiner

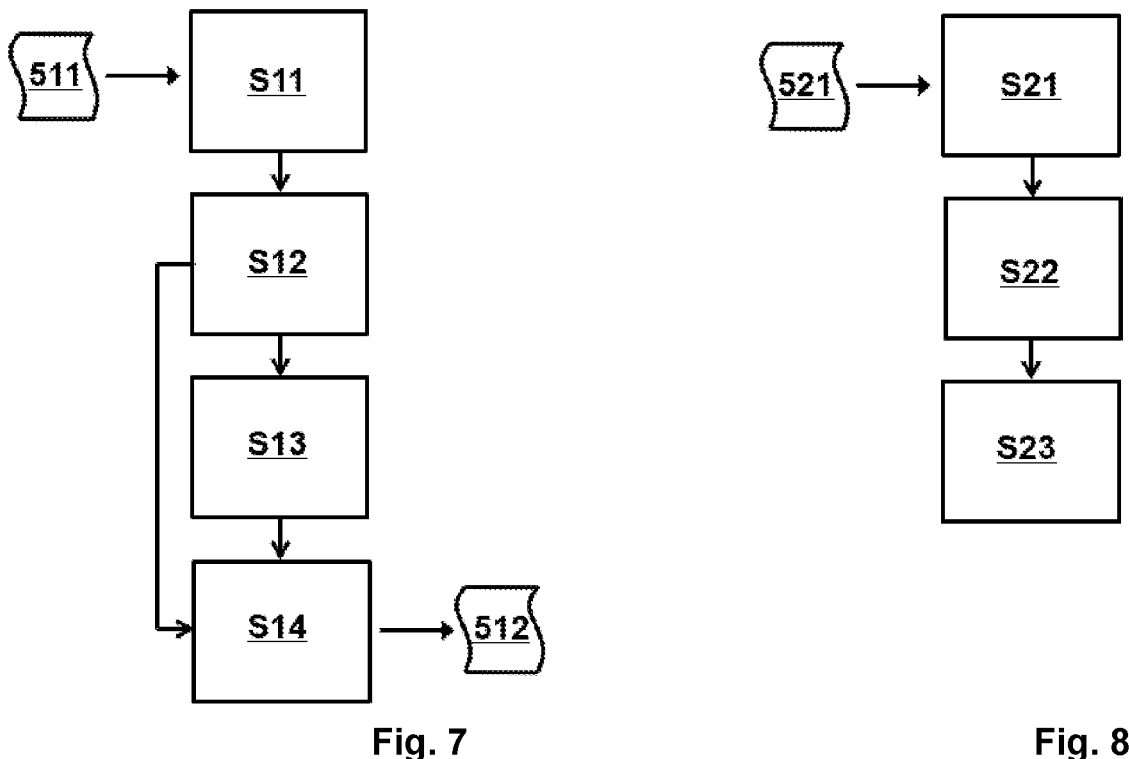
Fig. 7                                            Fig. 8
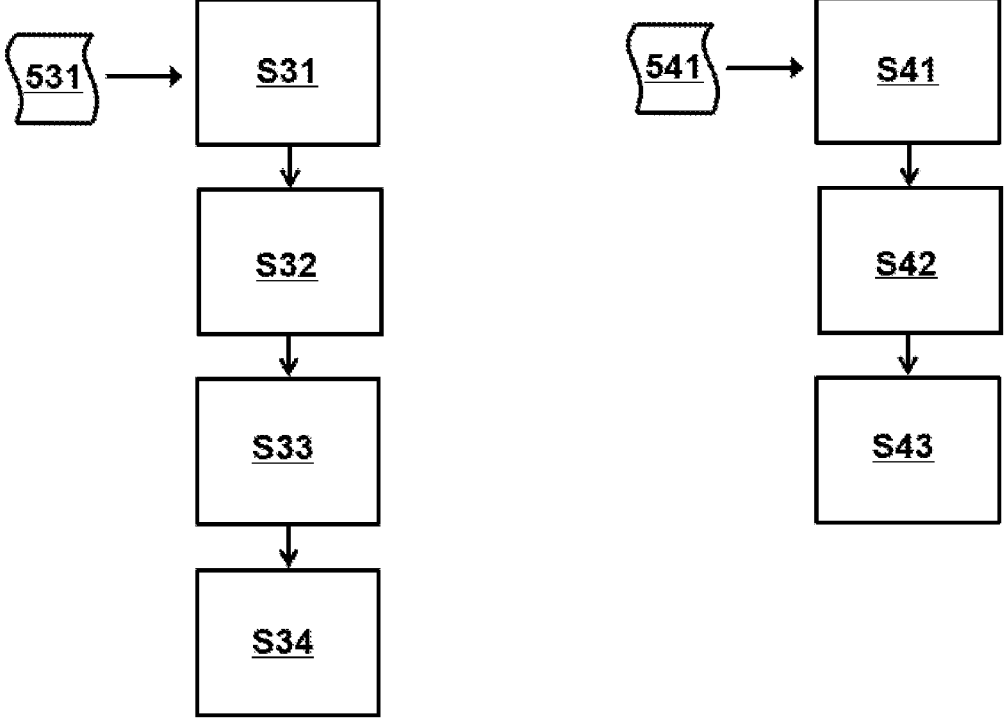
Fig. 9                                            Fig. 10

OPERATING A HEARING DEVICE TO ASSIST THE USER IN ENGAGING IN A HEALTHY LIVING STYLE

RELATED APPLICATIONS

The present application claims priority to EP Patent Application No. 22212819.1, filed Dec. 12, 2022, the contents of which are hereby incorporated by reference in their entirety.

BACKGROUND INFORMATION

Hearing devices may be used to improve the hearing capability or communication capability of a user, for instance by compensating a hearing loss of a hearing-impaired user, in which case the hearing device is commonly referred to as a hearing instrument such as a hearing aid, or hearing prosthesis. A hearing device may also be used to output sound based on an audio signal which may be communicated by a wire or wirelessly to the hearing device. A hearing device may also be used to reproduce a sound in a user's ear canal detected by an input transducer such as a microphone or a microphone array. The reproduced sound may be amplified to account for a hearing loss, such as in a hearing instrument, or may be output without accounting for a hearing loss, for instance to provide for a faithful reproduction of detected ambient sound and/or to add audio features of an augmented reality in the reproduced ambient sound, such as in a hearable. A hearing device may also provide for a situational enhancement of an acoustic scene, e.g. beamforming and/or active noise cancelling (ANC), with or without amplification of the reproduced sound. A hearing device may also be implemented as a hearing protection device, such as an earplug, configured to protect the user's hearing. Different types of hearing devices configured to be be worn at an ear include earbuds, earphones, hearables, and hearing instruments such as receiver-in-the-canal (RIC) hearing aids, behind-the-ear (BTE) hearing aids, in-the-ear (ITE) hearing aids, invisible-in-the-canal (IIC) hearing aids, completely-in-the-canal (CIC) hearing aids, cochlear implant systems configured to provide electrical stimulation representative of audio content to a user, a bimodal hearing system configured to provide both amplification and electrical stimulation representative of audio content to a user, or any other suitable hearing prostheses. A hearing system comprising two hearing devices configured to be worn at different ears of the user is sometimes also referred to as a binaural hearing device. A hearing system may also comprise a hearing device, e.g., a single monaural hearing device or a binaural hearing device, and a user device, e.g., a smartphone and/or a smartwatch, communicatively coupled to the hearing device.

Hearing devices are often employed in conjunction with communication devices, such as smartphones or tablets, for instance when listening to sound data processed by the communication device and/or during a phone conversation operated by the communication device. More recently, communication devices have been integrated with hearing devices such that the hearing devices at least partially comprise the functionality of those communication devices. A hearing system may comprise, for instance, a hearing device and a communication device.

In recent times, some hearing devices are also increasingly equipped with different sensor types. Traditionally, those sensors often include a sound sensor to detect a sound and to output an amplified and/or signal processed version of the sound to the user. In an effort to provide the user with even more information about himself and/or the ambient environment, various other sensor types are progressively implemented, in particular sensors which are not directly related to the sound reproduction and/or amplification function of the hearing device. Those sensors include inertial sensors, such as accelerometers, allowing to monitor the user's movements. Physiological sensors, such as optical sensors and bioelectric sensors, are mostly employed for monitoring the user's health.

Hearing impairment is often paired with other health risks. Those hearing loss comorbidities can affect the physical health, e.g., an increased risk of cardiovascular disease, dehydration, diabetes, stumbling or falling during walking, visual impairment, sleep deprivation, and insufficient bodily hygiene. Further, the mental health of a hearing device user can be affected, e.g., social isolation, unhappiness, depressive symptoms, and cognitive decline. Those health risks could be reduced or mitigated by the user, at least to a certain extent, by engaging in a healthier living style. However, often the user is not aware or tends to ignore daily opportunities to improve his health. Especially older users tend to be stuck in their daily routine and find it hard to adopt a new behavior benefiting their health situation.

For example, a user suffering from dehydration could decrease the risk by increasing his fluid intake but may instead stick to his habit of not drinking enough. A user feeling unhappy or depressed may improve his mood by directing his awareness to a subject in his environment suitable to lighten him up but may instead be distracted coping with inner negative emotions. A user living in social isolation could improve his situation by taking opportunities to engage in conversations with other people but may instead choose to ignore those possibilities to meet people or to strengthen relationships with acquaintances. A user neglecting his body hygiene such as his oral care could improve on that by brushing his teeth more carefully and/or more regularly but may not feel inclined to do so out of habit. A user at risk of a cardiovascular disease could improve his fitness by regularly exercising but may postpone or forget about it in his daily routine. A user suffering from sleep deprivation could take precautions making it easier to him falling asleep, e.g., by tuning down a disturbing sound before going to bed, but may not take those measures by force of habit or for convenience.

BRIEF DESCRIPTION OF THE DRAWINGS

Reference will now be made in detail to embodiments, examples of which are illustrated in the accompanying drawings. The drawings illustrate various embodiments and are a part of the specification. The illustrated embodiments are merely examples and do not limit the scope of the disclosure. Throughout the drawings, identical or similar reference numbers designate identical or similar elements. In the drawings:

FIGS. 7-10 schematically illustrate some exemplary methods of processing an input audio signal to assist the user in engaging in a healthy living style.

DETAILED DESCRIPTION

Figure 1:
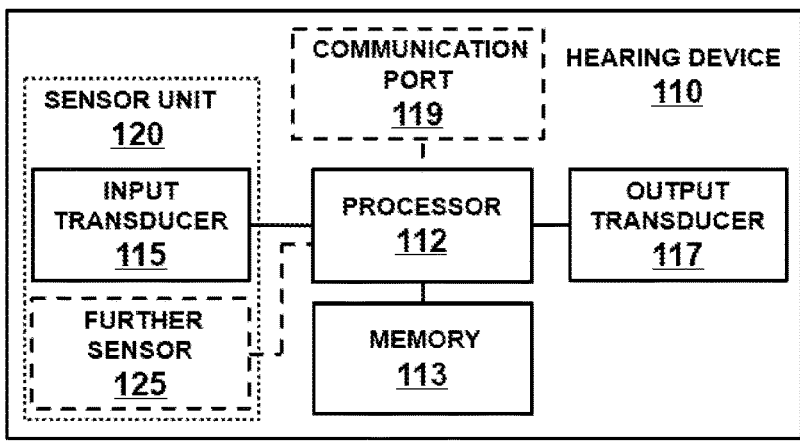
FIG. 1 schematically illustrates an exemplary hearing device.

The disclosure relates to a method of operating a hearing device configured to be worn at an ear of a user to assist the user in engaging in a healthy living style. The disclosure also relates to a hearing device for performing the method and a computer-readable medium storing instructions for performing the method.

It is a feature of the present disclosure to avoid at least one of the above mentioned disadvantages and to propose a method of operating a hearing device which assists the user in engaging in a healthier living style, in particular relative to a subject in the user's environment which is suitable to impact the physical and/or mental health of the user. It is another feature that such a subject can be more easily recognized by the user and/or that an awareness of the user of the subject can be increased. It is a further feature that a desire of the user to utilize the subject or a subject of a corresponding type and/or to engage in an activity involving the subject or a subject of a corresponding type is enhanced. It is a further feature that a subject potentially harmful for the user's health can be more easily ignored by the user and/or faded out from the user's consciousness and/or consciousness. It is another feature to achieve at least one of the above mentioned features by employing a sound emitted by the subject. It is another feature to address a specific aspect of the user's health, in particular at least one of the aspects addressed further below. It is a further feature to recognize a living situation of the user in which assisting the user in engaging in the healthier living style, in particular relative to the specific health aspect, is beneficial for the user and to assist the user in such a situation. It is another feature to propose a hearing device and/or a computer implemented medium having at least one of these advantages.

At least one of these features can be achieved by a method of providing an alert for a user comprising the features described herein and/or a hearing device comprising the features described herein and/or a computer-readable medium comprising the features described herein.

Accordingly, the present disclosure proposes a method of operating a hearing device configured to be worn at an ear of a user to assist the user in engaging in a healthy living style, the method comprising receiving, from an input transducer included in the hearing device, input audio signal indicative of a sound detected in the environment;

processing the input audio signal;

outputting, by an output transducer included in the hearing device, an output audio signal based on the processed input audio signal so as to stimulate the user's hearing;

determining whether the input audio signal comprises an audio feature matching a sound pattern characteristic of sound emitted by a subject suitable to impact a physical and/or mental health of the user; and, when the input audio signal comprises the audio feature, modifying, during the processing of the input audio signal, the audio feature in the input audio signal so as to increase or decrease, during the outputting of the output audio signal, an awareness of the user of a presence of the subject in the environment.

In particular, by the modifying of the audio feature in the input audio signal, a perception of the audio feature in the output audio signal can be facilitated or impeded for the user relative to a perception of the sound emitted by the subject in the detected sound. In this way, the user can be assisted into engaging into the healthier living style by way of evoking his increased or decreased awareness relative to the subject suitable for impacting the user's health.

Independently, the present disclosure proposes a hearing device configured to be worn at an ear of a user, the hearing device comprising an input transducer configured to provide an input audio signal indicative of a sound detected in the environment of the user, a processor, and an output transducer configured to output an output audio signal, wherein the processor is configured to perform the method.

Independently, the present disclosure proposes a hearing system comprising a hearing device configured to be worn at an ear of a user and a communication device communicatively coupled to the hearing device, the hearing device comprising an input transducer configured to provide an input audio signal indicative of a sound detected in the environment of the user, and an output transducer configured to output an output audio signal, wherein the hearing device and/or the communication device comprises a processor configured to perform the method.

Independently, the present disclosure proposes a non-transitory computer-readable medium storing instructions that, when executed by a processor included in a hearing device, cause the hearing device to perform operations of the method Subsequently, additional features of some implementations of the method of operating the hearing device and/or the hearing device and/or the computer-readable medium are described. Each of those features can be provided solely or in combination with at least another feature. The features can be correspondingly provided in some implementations of the method and/or the hearing device and/or the computer-readable medium.

In some implementations, during the determining whether the input audio signal comprises the audio feature, the input audio signal is input into a machine learning algorithm which separates the audio feature from the input audio signal and/or outputs a likelihood that the input audio signal comprises the audio feature, wherein the machine learning algorithm has been trained with previously recorded input audio signal characteristic of the sound emitted by the subject. In some instances, the sound samples may be recorded from the subject and/or one or more other subjects of a corresponding type suitable to impact the physical and/or mental health of the user.

In some implementations, after the determining whether the input audio signal comprises the audio feature, the machine learning algorithm is trained with the input audio signal and/or the audio feature matching the sound pattern when it is determined that the input audio signal comprises the audio feature matching the sound pattern.

In some implementations, the method further comprises receiving user control data indicative of whether the user desires said modifying of the audio feature, wherein the determining whether the input audio signal comprises the audio feature and/or the modifying of the audio feature in the input audio signal is performed depending on the user control data.

In some instances, the user control data may be received from a user interface. The user interface may be provided by the hearing device and/or a communication device communicatively coupled to the hearing device. For instance, the user interface may be provided as a push button and/or a touch screen allowing the user to enter a command whether he desires said modifying of the audio feature. The user interface may also be provided by speech recognition of the voice of the user, e.g., when detected by the input transducer, allowing the user to enter the command whether he desires said modifying of the audio feature. The command entered by the user via the user interface can thus be converted in the user control data.

In some implementations, the subject is of a type of subjects which are each suitable to impact an equal aspect of the physical and/or mental health of the user, wherein at least part of the subjects of the type emit a different sound and the sound pattern is characteristic of the different sound emitted by different subjects. In some instances, the sound pattern may be characteristic of the sound emitted by a plurality of the subjects of the type emitting a different sound. In some instances, the sound pattern may be characteristic of the sound emitted by each of the subjects of the type. In some instances, the processing unit is configured to determine that the input audio signal comprises the audio feature matching the sound pattern when the sound emitted from one or more of the subjects of the type is detected in the environment.

In some implementations, the aspect of the physical and/or mental health of the user includes
  a drinking and/or eating behavior of the user; and/or
  a mood of the user; and/or
  a social activity of the user; and/or
  a sleeping behavior of the user; and/or
  a nervousness and/or emotional stress of the user; and/or
  a physical activity of the user; and/or
  a tooth brushing behavior of the user.

In some implementations, the method further comprises receiving, from a user interface, user control data indicative of one or more said aspects of the physical and/or mental health of the user which the user desires to engage in, wherein the determining whether the input audio signal comprises the audio feature and/or the modifying of the audio feature in the input audio signal is performed depending on the user control data. In some instances, the user control data may be received from a user interface. The user interface may be provided at the hearing device and/or a communication device communicatively coupled to the hearing device. For instance, the user interface may be provided as a push button and/or a touch screen allowing the user to select one or more aspects of the physical and/or mental health which he desires to engage in. The user interface may also be provided by speech recognition of the voice of the user, e.g., when detected by the input transducer, allowing the user to select by speech one or more aspects of the physical and/or mental health which he desires to engage in. The selection of one or more aspects of the physical and/or mental health entered by the user via the user interface can thus be converted in the user control data.

In some implementations, the method further comprises receiving sensor data including
    said input audio signal; and/or
    physiological data indicative of a physiological property of the user; and/or movement data indicative of a movement performed by the user; and/or
    interaction data indicative of an interaction of the user with a user interface,
  monitoring, based on the sensor data, a parameter indicative of the physical and/or mental health of the user; and
  determining whether the parameter fulfills a condition, wherein the determining whether the input audio signal comprises the audio feature and/or the modifying of the audio feature in the input audio signal is performed depending on the condition being fulfilled by the sensor data.

In some implementations, the sensor data is indicative of the aspect of the physical and/or mental health of the user and the condition is determined to be fulfilled when said aspect of the physical and/or mental health of the user is determined to be below a threshold. For example, the threshold may be representative of a critical value of the drinking and/or eating behavior of the user and/or mood of the user and/or social activity of the user and/or physical activity of the user and/or nervousness and/or emotional stress of the user and/or sleeping behavior of the user and/or tooth brushing behavior of the user.

In some implementations, the physiological data is received from
  an optical sensor configured to emit the light at a wavelength absorbable by an analyte contained in blood of the user; and/or
  a bioelectric sensor comprising at least one electrode configured to detect a bioelectric signal from the user's body.

In some implementations, the optical sensor configured to emit the light at a wavelength absorbable by an analyte contained in blood such that the physiological sensor data included in the optical sensor data comprises information about the blood flowing through tissue at the ear. In some implementations, the optical sensor is configured as a photoplethysmography (PPG) sensor such that the physiological sensor data included in optical sensor data comprises PPG data, e.g. a PPG waveform. In some implementations, the bioelectric sensor comprises a skin impedance sensor and/or an electrocardiogram (ECG) sensor and/or an electroencephalogram (EEG) sensor and/or an electrooculography (EOG) sensor.

In some implementations, the sound pattern is characteristic of
  a sound of opening a receptacle; and/or
  a sound of pouring and/or flowing and/or splashing water, e.g., a sound of pouring a drink and/or a sound of pouring rain and/or a sound of waves in a lake and/or ocean and/or a sound of water running through a river and/or a sound occurring when taking a shower and/or a bath and/or when swimming, and/or the like; and/or
  a sound related to food preparation and/or food consumption, e.g., a sound of cutting vegetables and/or cooking a meal and/or chewing food; and/or
  a motor sound; and/or
  a sound typically occurring in a natural and/or rural environment; and/or
  a sound of a wild animal, e.g., a chirping of birds and/or crickets, a roaring of an elk and/or lion, and/or the like; and/or
  a sound of a domesticated animal, e.g., a mooing of a cow, a mewing of a cat, a barking of a dog, and/or the like; and/or
  a sound of a baby; and/or a sound of human laughter and/or giggling; and/or a sound of crackling fire; and/or a sound of blowing wind; and/or a sound of a music instrument and/or a singing voice; and/or a sound of a communication between humans; and/or a sound of a household appliance; and/or a sound of traffic noise and/or factory noise; and/or a voice of a significant other; and/or a sound of footsteps; and/or a sound related to people performing a physical activity, e.g., a sound of running and/or cycling and/or weight lifting and/or intense breathing and/or the like; and/or a sound of tooth brushing.

In some implementations, when the aspect of the physical and/or mental health of the user concerns the drinking behavior of the user, in particular a hydration level of the user and/or a state of dehydration, the sound pattern is characteristic of a sound of opening a receptacle and/or a sound of pouring and/or flowing and/or splashing water.

In some implementations, when the aspect of the physical and/or mental health of the user concerns the eating behavior of the user, in particular an unbalanced and/or inferior eating behavior of the user and/or a state of malnutrition, the sound pattern is characteristic of a sound related to food preparation and/or food consumption.

In some implementations, when the aspect of the physical and/or mental health of the user concerns the mood of the user, in particular a level of happiness or unhappiness and/or a state of depression, the sound pattern is characteristic of a sound of opening a receptacle and/or a sound of pouring and/or flowing and/or splashing water and/or a sound related to food preparation and/or food consumption and/or a motor sound and/or a sound typically occurring in a natural and/or rural environment and/or a sound of a wild animal and/or a sound of a domesticated animal and/or a sound of a baby and/or a sound of human laughter and/or giggling and/or a sound of crackling fire and/or a sound of blowing wind and/or a sound of a music instrument and/or a singing voice and/or a sound of a communication between humans and/or a voice of a significant other and/or a sound of footsteps and/or a voice of a significant other and/or a sound of footsteps and/or a sound of tooth brushing.

In some implementations, when the aspect of the physical and/or mental health of the user concerns the social activity of the user, in particular a level of social isolation and/or a state of loneliness, the sound pattern is characteristic of a sound of a communication between humans and/or a voice of a significant other and/or a sound of footsteps and/or a sound related to people performing a physical activity and/or a voice of a significant other.

In some implementations, when the aspect of the physical and/or mental health of the user concerns a nervousness and/or emotional stress of the user, the sound pattern is characteristic of a sound of opening a receptacle and/or a sound of pouring and/or flowing and/or splashing water and/or a sound related to food preparation and/or food consumption and/or a motor sound and/or a sound typically occurring in a natural and/or rural environment and/or a sound of a wild animal and/or a sound of a domesticated animal and/or a sound of a baby and/or a sound of human laughter and/or giggling and/or a sound of crackling fire and/or a sound of blowing wind and/or a sound of a music instrument and/or a singing voice and/or a sound of a communication between humans and/or a voice of a signifi-cant other and/or a sound of footsteps and/or a sound of tooth brushing.

In some implementations, when the aspect of the physical and/or mental health of the user concerns a physical activity of the user, in particular a fitness level and/or a lack of exercise, the sound pattern is characteristic of a sound of footsteps and/or a sound related to people performing a physical activity.

In some implementations, when the aspect of the physical and/or mental health of the user concerns a tooth brushing behavior of the user, in particular an insufficient level and/or a lack of dental hygiene, the sound pattern is characteristic of a sound of tooth brushing.

In some implementations, when the aspect of the physical and/or mental health of the user concerns a drinking and/or eating behavior of the user and/or a mood of the user and/or a social activity of the user and/or a nervousness and/or emotional stress of the user and/or a physical activity of the user and/or a body hygiene of the user, in particular a tooth brushing behavior of the user, the input audio signal is modified in the input audio signal such that an awareness of the user of a presence of the subject in the environment is increased. In particular, the input audio signal may be modified by augmenting the audio feature in the input audio signal such that, during the outputting of the audio signal, a perception of the augmented audio feature in the output audio signal is facilitated for the user relative to a perception of the sound emitted by the subject in the detected sound.

In some implementations, when the aspect of the physical and/or mental health of the user concerns a sleeping behavior of the user, in particular an insufficient amount of sleep and/or a sleep deprivation and/or a nervousness and/or emotional stress of the user, the sound pattern is character-istic of a sound of a household appliance and/or a sound of traffic noise and/or factory noise and/or a sound of a baby.

In some implementations, when the aspect of the physical and/or mental health of the user concerns a sleeping behavior of the user and/or a nervousness and/or emotional stress of the user, the input audio signal is modified in the input audio signal such that an awareness of the user of a presence of the subject in the environment is decreased. In particular, the input audio signal may be modified by fading and/or suppressing the audio feature in the input audio signal such that, during the outputting of the audio signal, a perception of the modified audio feature in the output audio signal is impeded for the user relative to a perception of the sound emitted by the subject in the detected sound.

In some implementations, the method further comprises receiving context data including location data indicative of a current location of the user; and/or time data indicative of a current time; and determining whether the context data fulfills a condition, wherein the determining whether the input audio signal comprises the audio feature and/or the modifying of the audio feature in the input audio signal is performed depending on the condition being fulfilled by the con-text data.

In some implementations, the condition is determined to be fulfilled when a current location of the user and/or current time, as indicated by the context data, matches a predeter-mined location and/or time. To illustrate, the engaging of the user in a healthy living style may thus be restricted to the predetermined location and/or time at which it can be more beneficial to the user.

In some implementations, said modifying the audio fea-ture in the input audio signal comprises determining, based on the audio feature, a location of the subject associated with the sound pattern, and directing a beamformer toward the location; and/or increasing or decreasing a sharpness of the audio feature; and/or increasing or decreasing a volume of the audio feature; and/or altering a frequency of the audio feature; and/or suppressing the audio feature;

increasing a number of times in which the audio feature is included in the audio signal; and/or extracting the audio feature from the audio signal, altering a property of the audio feature, and adding the audio feature with the altered property to the audio signal; and/or superimposing, wherein said audio feature is a first audio feature, a second audio feature on the input audio signal, in particular at a time at which said first audio feature occurs.

In some implementations, the second audio feature superimposed on the first audio feature may be an audible audio feature, in particular such that the second audio feature is consciously perceivable by the user. In some implementations, the second audio feature superimposed on the first audio feature may be a subliminal audio feature, in particular such that the second audio feature is only subconsciously perceivable by the user.

In some implementations, said modifying the audio feature in the input audio signal comprises augmenting the audio feature in the input audio signal. In this way, an awareness of the user of a presence of the subject in the environment can be increased during the outputting of the output audio signal, in particular such that a perception of the audio feature in the output audio signal can be facilitated for the user relative to a perception of the sound emitted by the subject in the detected sound. The augmenting may comprise at least one of said directing a beamformer and/or increasing a sharpness and/or increasing a volume and/or altering a frequency of the audio feature and/or increasing a number of times in which the audio feature is included in the audio signal and/or extracting and altering a property of the audio feature and/or superimposing a second audio feature in the input audio signal.

In some implementations, said modifying the audio feature in the input audio signal comprises fading and/or suppressing the audio feature in the input audio signal. In this way, an awareness of the user of a presence of the subject in the environment can be decreased during the outputting of the output audio signal, in particular such that a perception of the audio feature in the output audio signal can be impeded for the user relative to a perception of the sound emitted by the subject in the detected sound. The fading and/or suppressing may comprise at least one of said decreasing a sharpness and/or decreasing a volume and/or altering a frequency of the audio feature and/or superimposing a second audio feature in the input audio signal. In particular, the second audio feature may be less perceivable than the first audio feature.

FIG. 1 illustrates an exemplary hearing device 110 configured to be worn at an ear of a user.

Hearing device 110 may be implemented by any type of hearing device configured to enable or enhance hearing or a listening experience of a user wearing hearing device 110. For example, hearing device 110 may be implemented by a hearing aid configured to provide an amplified version of audio content to a user, a sound processor included in a cochlear implant system configured to provide electrical stimulation representative of audio content to a user, a sound processor included in a bimodal hearing system configured to provide both amplification and electrical stimulation representative of audio content to a user, or any other suitable hearing prosthesis, or an earbud or an earphone or a hearable.

Different types of hearing device 110 can also be distinguished by the position at which they are worn at the ear. Some hearing devices, such as behind-the-ear (BTE) hearing aids and receiver-in-the-canal (RIC) hearing aids, typically comprise an earpiece configured to be at least partially inserted into an ear canal of the ear, and an additional housing configured to be worn at a wearing position outside the ear canal, in particular behind the ear of the user. Some other hearing devices, as for instance earbuds, earphones, hearables, in-the-ear (ITE) hearing aids, invisible-in-the-canal (IIC) hearing aids, and completely-in-the-canal (CIC) hearing aids, commonly comprise such an earpiece to be worn at least partially inside the ear canal without an additional housing for wearing at the different ear position.

As shown, hearing device 110 includes a processor 112 communicatively coupled to a memory 113, an input transducer 115, and an output transducer 117. Hearing device 110 may include additional or alternative components as may serve a particular implementation. Input transducer 115 may be implemented by any suitable device configured to detect sound in the environment of the user and to provide an input audio signal indicative of the detected sound, e.g., a microphone or a microphone array. Output transducer 117 may be implemented by any suitable audio transducer configured to output an output audio signal to the user, for instance a receiver of a hearing aid, an output electrode of a cochlear implant system, or a loudspeaker of an earbud.

Memory 113 may be implemented by any suitable type of storage medium and is configured to maintain, e.g. store, data controlled by processor 112, in particular data generated, accessed, modified and/or otherwise used by processor 112. For example, memory may be configured to store instructions used by processor 112 to process the input audio signal received from input transducer 115, e.g., one or more audio processing programs. As another example, memory 113 may be configured to store instructions to determine a property of the input audio signal, e.g., whether the audio signal comprises an audio feature matching a sound pattern. The instructions may include a database of a plurality of different sound patterns which may be accessed by processor 112 as required. Memory 113 may comprise a non-volatile memory from which the maintained data may be retrieved even after having been power cycled, for instance a flash memory and/or a read only memory (ROM) chip such as an electrically erasable programmable ROM (EEPROM). A non-transitory computer-readable medium may thus be implemented by memory 113. Memory 113 may further comprise a volatile memory, for instance a static or dynamic random access memory (RAM).

Processor 112 is configured to receive, from input transducer 115, an input audio signal indicative of a sound detected in the environment of the user; to determine whether the input audio signal comprises an audio feature matching a sound pattern characteristic of sound emitted by a subject suitable to impact a physical and/or mental health of the user; and, when the input audio signal comprises the audio feature, to modify the audio feature in a processing of the input audio signal so as to increase or decrease, during the outputting of the audio signal, an awareness of the user of a presence of the subject in the environment. Based on the processed input audio signal, an output audio signal can then be output by output transducer 117. These and other operations, which may be performed by processor 112, are described in more detail in the description that follows.

As illustrated, hearing device 110 may further comprise a communication port 119. Communication port 119 may be implemented by any suitable data transmitter and/or data receiver and/or data transducer configured to exchange data with another device. For instance, the other device may be another hearing device configured to be worn at the other ear of the user than hearing device 110 and/or a communication device such as a smartphone, smartwatch, tablet and/or the like.

Communication port 119 may be configured for wired and/or wireless data communication. For instance, data may be communicated in accordance with a Bluetooth™ protocol and/or by any other type of radio frequency (RF) communication.

Figure 2:
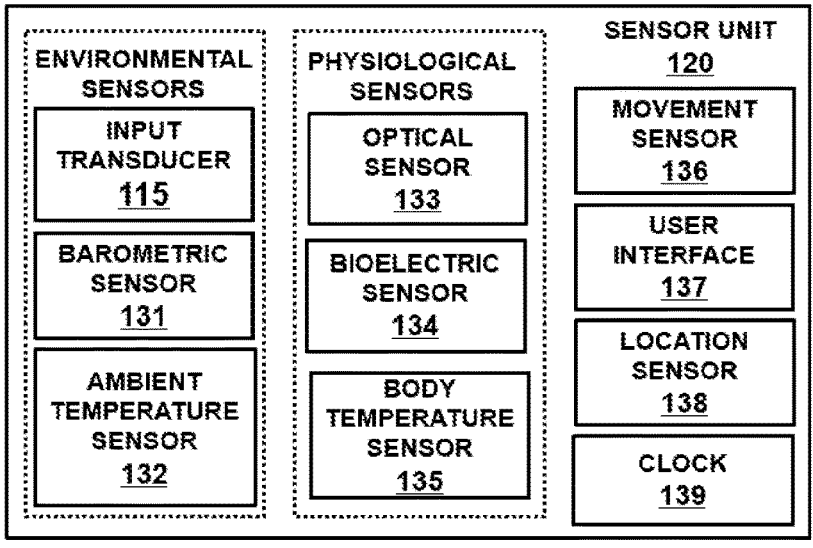
FIG. 2 schematically illustrates an exemplary sensor unit comprising one or more sensors which may be implemented in the hearing device illustrated in FIG. 1.

As illustrated, hearing device 110 may also comprise at least one further sensor 125 communicatively coupled to processor 112 in addition to input transducer 115. A sensor unit 120 may comprise input transducer 115 and the at least one further sensor 125. Some examples of a sensor which may be implemented in sensor unit 120 in place of sensor 125 are illustrated in FIG. 2.

Sensor unit 120 may include at least one environmental sensor configured to provide environmental data indicative of a property of the environment of the user in addition to input transducer 115, for example a barometric sensor 131 and/or an ambient temperature sensor 132. Sensor unit 120 may include at least one physiological sensor configured to provide physiological data indicative of a physiological property of the user, for example an optical sensor 133 and/or a bioelectric sensor 134 and/or a body temperature sensor 135. Optical sensor 133 may be configured to emit the light at a wavelength absorbable by an analyte contained in blood such that the physiological sensor data comprises information about the blood flowing through tissue at the ear. E.g., optical sensor 133 can be configured as a photoplethysmography (PPG) sensor such that the physiological sensor data comprises PPG data, e.g. a PPG waveform. Bioelectric sensor 134 may be implemented as a skin impedance sensor and/or an electrocardiogram (ECG) sensor and/or an electroencephalogram (EEG) sensor and/or an electrooculography (EOG) sensor.

Sensor unit 120 may include a movement sensor 136 configured to provide movement data indicative of a movement of the user, for example an accelerometer and/or a gyroscope. Sensor unit 120 may include a user interface 137 configured to provide interaction data indicative of an interaction of the user with hearing device 110, e.g., a touch sensor and/or a push button. Sensor unit 120 may include at least one location sensor 138 configured to provide location data indicative of a current location of the user, for instance a GPS sensor. Sensor unit 120 may include at least one clock 139 configured to provide time data indicative of a current time. Context data may be defined as data indicative of a local and/or temporal context of the data provided by other sensors 115, 131-137. Context data may comprise the location data and/or the time data provided by location sensor 138 and/or clock 139. Context data may also be received from an external device via communication port 119, e.g., from a communication device. Sensor unit 120 may include further sensors providing sensor data indicative of a property of the user and/or the environment and/or the context.

Figure 3:
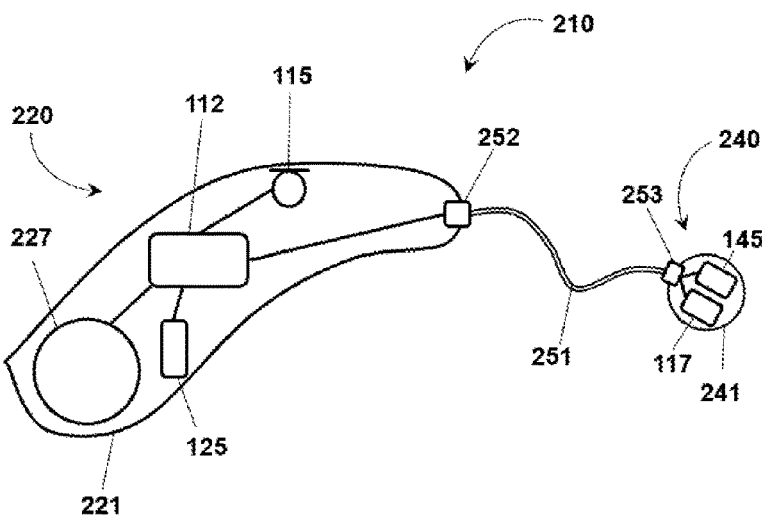
FIG. 3 schematically illustrates an embodiment of the hearing device illustrated in FIG. 1 as a RIC hearing aid.

FIG. 3 illustrates an exemplary implementation of hearing device 110 as a RIC hearing aid 210. RIC hearing aid 210 comprises a BTE part 220 configured to be worn at an ear at a wearing position behind the ear, and an ITE part 240 configured to be worn at the ear at a wearing position at least partially inside an ear canal of the ear. BTE part 220 comprises a BTE housing 221 configured to be worn behind the ear. BTE housing 221 accommodates processor 112 communicatively coupled to input transducer 115 and further sensor 125. BTE part 220 further includes a battery 227 as a power source. ITE part 240 is an earpiece comprising an ITE housing 241 at least partially insertable in the ear canal. ITE housing 241 accommodates output transducer 117 and another sensor 241, which may include any of sensors 115, 131-139. Sensor unit 120 of exemplary RIC hearing aid 210 thus comprises input transducer 115 and sensors 125, 245. BTE part 220 and ITE part 240 are interconnected by a cable 251. Processor 112 is communicatively coupled to output transducer 117 and sensor 245 of ITE part 240 via cable 251 and cable connectors 252, 253 provided at BTE housing 221 and ITE housing 241.

Figure 4:
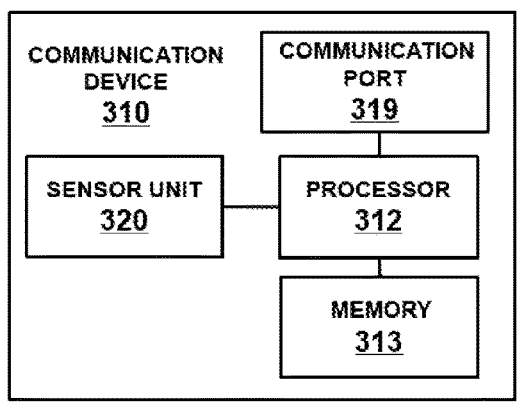
FIG. 4 schematically illustrates a communication device which may be communicatively coupled to the hearing device illustrated in FIG. 1.

FIG. 4 illustrates an exemplary communication device 310 configured to be operated remote from the ear at which hearing device 110 is worn. For instance, communication device 310 may be implemented as an electronic device portable by the user, e.g., a smartphone, smartwatch, tablet, or the like. A hearing system may comprise hearing device 110 and communication device 310 communicatively coupled to hearing device 110.

In the illustrated example, communication device 310 includes a processor 312 communicatively coupled to a memory 313, a sensor unit 320, and a communication port 319.

Memory 313 may be implemented corresponding to memory 113 described above. Sensor unit 320 may include one or more sensors corresponding to sensors 115, 131-137 of sensor unit 120 described above. Communication port 319 may be implemented corresponding to communication port 119 described above. Processor 112 of hearing device 110 and processor 312 of communication device 310 can thus be communicatively coupled via communication ports 319. E.g., sensor data provided by sensor units 120, 315 may thus be communicated between processors 112, 312. A processing unit may comprise processor 112 of hearing device 110 and processor 312 of communication device 310. The processing unit may be implemented, for instance, as a distributed processing system of processors 112, 312 and/or in a master/slave configuration of processors 112, 312.

Figure 5:
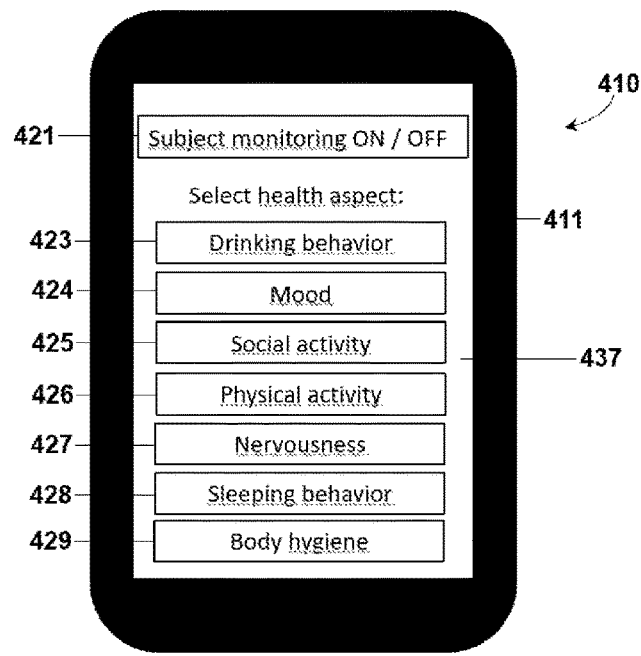
FIG. 5 schematically illustrates an embodiment of the communication device illustrated in FIG. 4 comprising a user interface allowing the user to enter user control data for the hearing device to assist him in engaging in a healthy living style.

FIG. 5 illustrates an exemplary implementation of communication device 310 as a portable device 410, e.g., a smartphone, smartwatch, or a tablet. Portable device 410 comprises a portable housing 411. Portable device 410 further comprises a user interface 437 allowing the user to enter a user command which can be received by processor 112 of hearing device 110 and/or processor 312 of communication device 310 as user control data. User interface 437 may be implemented in sensor unit 320 as described above. For instance, as illustrated, user interface 437 may be implemented as a touch screen. In other examples, the user interface may be implemented by speech recognition allowing the user to enter a command with his voice.

In the illustrated example, user interface 437 comprises a plurality of push buttons 421, 423, 424, 425, 426, 427, 428, 429. Push button 421 allows the user to enter a user command whether the user desires a modifying of an audio feature contained in the input audio signal matching a sound pattern characteristic of sound emitted by a subject in his environment suitable to impact a physical and/or mental health of the user. By the modifying of the audio feature, a perception of the audio feature in the output audio signal can be facilitated or impeded for the user relative to a perception of the sound emitted by the subject in the detected sound. In this way, the user can be assisted into engaging into a healthier living style by way of evoking his increased or decreased awareness relative to the subject suitable for impacting his health.

Push buttons 423-426 allow the user to select one or more aspects of his physical and/or mental health which he wishes to improve. Push buttons 423, 426, 428, 429 relate to the physical health of the user. Push buttons 424, 425, 427 relate to the mental health of the user. Push button 423 relates to the drinking behavior of the user. To illustrate, a user suffering from dehydration could decrease the risk by increasing his fluid intake. Modifying, in particular augmenting, an audio feature contained in the input audio signal matching a sound pattern characteristic of sound emitted by a sound of opening a receptacle and/or a sound of pouring and/or flowing and/or splashing water could thus draw the user's attention to a source of fluid intake and/or remind the user that he should increase his fluid intake and/or increase the user's desire to drink something.

Push button 424 relates to the mood of the user. To illustrate, a user feeling unhappy or depressed may improve his mood by directing his awareness to a subject in his environment suitable to lighten him up or make him laugh or improve his mood. Modifying, in particular augmenting, an audio feature contained in the input audio signal matching a sound pattern characteristic of sound emitted by such a subject could draw the user's attention to the subject allowing him to focus on the subject distracting him from his unhappy thoughts. For instance, such a subject elevating the user's mood could be a wild animal emitting a sound in the user's environment, e.g., a chirping of birds and/or crickets, a roaring of an elk and/or lion, and/or a domesticated animal emitting a sound in the user's environment, e.g., a mooing of a cow, a mewing of a cat, a barking of a dog. Another example of a subject which could cheer the user up, e.g., when the user is interested in automobiles, is a motor which may be running in the user's environment and may emit a motor sound. To illustrate, the sound of the user's own car, e.g. a passenger car, determined in the input audio signal could be augmented in the output audio signal, e.g. to sound like a sports car, in order to improve the user's mood. Another example of a subject which could make the user laugh is another human laughing or giggling in the user's environment. Another example of a subject which could improve the user's mood is a sound of a baby and/or a voice of a significant and/or other human sounds such as a sound of footsteps. To illustrate, the voice of a user's friend determined in the input audio signal could be altered in the output audio signal, e.g. to sound funnier or more pleasing, in order to improve the user's mood. Other examples of subjects suitable to improve the user's happiness may include food, drinks, fire, wind, and/or the like.

Push button 425 relates to a social activity of the user. To illustrate, a user living in social isolation and/or feeling lonely could improve his situation by taking opportunities to engage in conversations with other people. Modifying, in particular augmenting, an audio feature contained in the input audio signal matching a sound pattern characteristic of a sound of a communication between humans and/or a voice of a significant other and/or a sound of footsteps and/or a sound related to people performing a physical activity and/or a voice of a significant other could thus increase the user's awareness of such opportunities in order to remind the user and/or awake the interest of the user to engage in such conversations.

Push button 426 relates to a physical activity of the user. To illustrate, a user suffering from a low fitness level and/or a lack of exercise and/or a user at risk of a cardiovascular disease could improve his situation by taking opportunities to engage more often in physical exercises. Modifying, in particular augmenting, an audio feature contained in the input audio signal matching a sound pattern characteristic of a sound related to other people performing a physical activity, e.g., a sound of running and/or cycling and/or weight lifting and/or intense breathing and/or footsteps, could contribute to the user's awareness of also improving his own fitness and could help him to identify situations for engaging in physical exercising.

Push button 427 relates to a nervousness and/or emotional stress of the user. To illustrate, a user being often nervous and/or stressed and/or anxious could improve his situation by directing his awareness to a subject in his environment suitable to calm him or to distract him and/or by reducing his awareness of a subject contributing to his nervousness and/or stress level and/or anxiousness.

Modifying an audio feature contained in the input audio signal matching a sound pattern characteristic of sound emitted by a subject suitable to calm the user or to distract the user may include, e.g., augmenting a sound of water such as pouring rain and/or waves in a lake and/or ocean and/or water running through a river and/or a sound occurring when taking a shower and/or a bath and/or when swimming. Other examples may include a sound typically occurring in a natural and/or rural environment and/or a sound of a wild animal and/or a sound of a domesticated animal and/or a sound of a baby and/or a sound of human laughter and/or giggling and/or a sound of crackling fire and/or a sound of blowing wind and/or a sound of a music instrument and/or a singing voice and/or a sound of a communication between humans and/or a voice of a significant other. Modifying an audio feature contained in the input audio signal matching a sound pattern characteristic of sound emitted by a subject contributing to his nervousness and/or stress level may include, e.g., fading and/or suppressing a sound of a household appliance and/or a sound of traffic noise and/or factory noise.

Push button 428 relates to a sleeping behavior of the user. To illustrate, a user suffering from sleep deprivation could take precautions making it easier to him falling asleep, e.g., by tuning down a disturbing sound before going to bed. Modifying, in particular fading or suppressing, an audio feature contained in the input audio signal matching a sound pattern characteristic of a subject exciting and/or irritating the user, e.g., a sound of a household appliance and/or a sound of traffic noise and/or factory noise, could help the user to calm down before going to bed and to fall easier asleep.

Push button 429 relates to a body hygiene of the user. To illustrate, a user neglecting his body hygiene such as his oral care could improve on that by brushing his teeth more carefully and/or more regularly. Modifying, in particular augmenting, an audio feature contained in the input audio signal matching a sound pattern characteristic of a sound of tooth brushing, e.g., a sound of a tooth brush sliding over teeth and/or a sound emitted by an electric toothbrush, could stimulate the user to clean his teeth for a prolonged time and/or more carefully and/or more often, e.g., by making the tooth brushing activity more fun.

Figure 6:
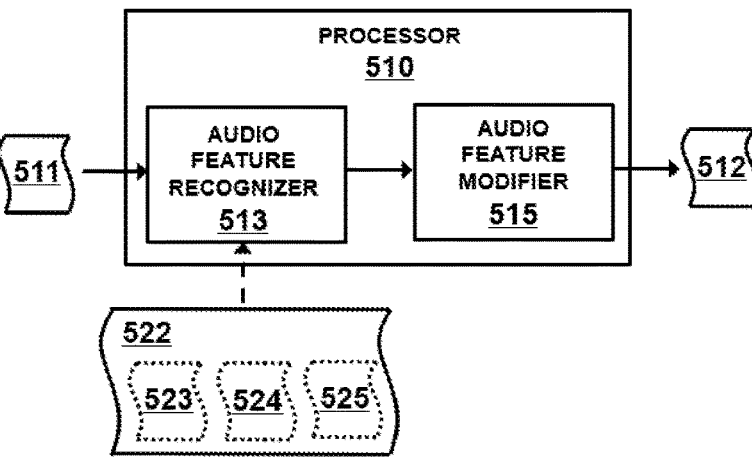
FIG. 6 schematically illustrates an exemplary algorithm of processing an input audio signal to assist the user in engaging in a healthy living style.

FIG. 6 illustrates a functional block diagram of an exemplary audio signal processing algorithm that may be executed by a processor 510. For instance, processor 510 may comprise processor 112 of hearing device 110 and/or processor 312 of communication device 310. In particular, the algorithm may be executed by one of processors 112, 312 or by both processors 112, 312, wherein processors 112, 312 form a processing unit. As shown, the algorithm is configured to be applied to an input audio signal 511 indicative of a sound detected in the environment of the user, which may be provided by input transducer 115. After a processing of input audio signal 511, the algorithm provides a processed input audio signal based on which an output audio signal 512 can be outputted by output transducer 117.

The algorithm comprises an audio feature recognition module 513 and an audio feature modification module 515. Input audio signal 511 is received by audio feature recognition module 513. Audio feature recognition module 513 is configured to determine whether input audio signal 511 comprises an audio feature matching a sound pattern characteristic of sound emitted by a subject suitable to impact a physical and/or mental health of the user. Input audio signal 511 is further received by audio feature modification module 515, at least when the input audio signal comprises the audio feature as determined by audio feature recognition module 513. Audio feature modification module 515 is configured to modify the audio feature in the input audio signal so as to increase or decrease, when output audio signal 512 based on the processed input audio signal is outputted by output transducer 117, an awareness of the user of a presence of the subject in the environment. The audio feature may be modified in the input audio signal such that a perception of the audio feature in the output audio signal can be facilitated or impeded for the user relative to a perception of the sound emitted by the subject in the detected sound as represented by input audio signal 511.

Audio feature recognition module 513 may be implemented as a machine learning algorithm which separates the audio feature from the input audio signal and/or outputs a likelihood that the input audio signal comprises the audio feature, wherein the machine learning algorithm has been trained with previously recorded input audio signals characteristic of the sound emitted by the subject. Some examples of such a machine learning algorithm, e.g., a neural network (DNN) or a plurality of neural networks, suitable to separate the audio feature from the input audio signal are disclosed in international patent application publications WO 2020/15234 A1 and WO 2020/15233 A1.

The previously recorded input audio signals, which may also be denoted as previously recorded audio samples, may be recorded from the subject and/or one or more other subjects of a corresponding type suitable to impact the physical and/or mental health of the user, in particular an equal aspect of the physical and/or mental health of the user. At least part of the subjects of a corresponding type may emit a different sound, wherein the sound pattern is characteristic of sound emitted by each of the subjects of the type. After the determining whether input audio signal 511 comprises the audio feature, the machine learning algorithm may be further trained with input audio signal 511 and/or the audio feature matching the sound pattern, when it is determined that input audio signal 511 comprises the audio feature matching the sound pattern.

As illustrated, different sound patterns 523, 524, 525 may be provided to audio feature recognition module 513. Sound patterns 523-525 may each be characteristic of sound emitted by a subject, or a type of subjects, suitable to impact a different aspect of the physical and/or mental health of the user. E.g., each of sound patterns 523-525 may be implemented as a different neural network or a different component of a neural network, which may be individually trained, as further described in WO 2020/15234 A1 and WO 2020/15233 A1, or a single neural network which has been trained to be representative of a plurality of sound patterns 523-525, as also described in WO 2020/15234 A1 and WO 2020/15233 A1. Sound patterns 523-525 may be stored in memory 113, 313, e.g., in the form of a database 522. Each of sound patterns 523-525 may thus be associated with a different aspect of the physical and/or mental health of the user. Audio feature modification module 515 may be configured to employ one or more of sound patterns 523-525, e.g., to retrieve one or more of sound patterns 523-525 from the memory, depending on which aspect of the physical and/or mental health of the user shall be addressed. E.g., a selection of one or more of sound patterns 523-525 by audio feature recognition module 513 may depend on user control data and/or sensor data and/or context data, as further described below.

Sound pattern 523-525 may be characteristic of sound emitted by a plurality of subjects which are of a type of subjects which are each suitable to impact an equal aspect of the physical and/or mental health of the user, wherein at least part of the subjects of the type emit a different sound and the sound pattern is characteristic of the different sound emitted by different subjects of the type. To illustrate, a sound of opening a receptacle may be different depending on the respective receptacle, wherein the sound pattern may be characteristic of the different sound emitted by different receptacles. A sound produced by an animal may be different for different animals, wherein the sound pattern may be characteristic of the different sound emitted by different animals. A sound emitted by different subjects of a type suitable to impact a mood of the user may be different, e.g., a motor sound of a sportscar and/or a motor sound of a passenger car and/or a motor sound of a bus, wherein the sound pattern may be characteristic of the different sound emitted by different subjects of the type.

Audio feature modification module 515 can be configured to modify the audio feature in the input audio signal depending on the aspect of the physical and/or mental health of the user which is intended to engage the user with, in particular depending on sound pattern 523-525 associated with the aspect of the physical and/or mental health of the user, which may be selected by audio feature recognition module 513.

For some aspects of the physical and/or mental health of the user, augmenting the audio feature input audio signal 511 can be desired, e.g., regarding a drinking and/or eating behavior of the user and/or a mood of the user and/or a social activity of the user and/or a physical activity of the user and/or a nervousness and/or emotional stress of the user and/or a tooth brushing behavior of the user. The augmenting may comprise, also depending on the aspect of the physical and/or mental health of the user, at least one of directing a beamformer toward the location of the subject and/or increasing a sharpness of the audio feature and/or increasing a volume of the audio feature and/or altering a frequency of the audio feature and/or increasing a number of times in which the audio feature is included in the audio signal and/or adding the audio feature with an altered property to the input audio signal and/or superimposing a second audio feature in input audio signal. E.g., when directing a beamformer toward the location of the subject, input transducer 115 may be implemented as a microphone array. Input audio signal 511 received from input transducer 115 may then be employed to determine the location of the subject suitable to impact a physical and/or mental health of the user in the environment, and input audio signal 511 may be modified to alter a directivity of input audio signal 511 toward the location of the subject.

For some aspects of the physical and/or mental health of the user, fading or suppressing the audio feature input audio signal 511 can be desired, e.g., regarding a sleeping behavior of the user and/or a nervousness and/or emotional stress of the user. The fading and/or suppressing may comprise at least one of said decreasing a sharpness of the audio feature and/or decreasing a volume of the audio feature and/or altering a frequency of the audio feature and/or adding the audio feature with an altered property to the input audio signal and/or superimposing a second audio feature in the input audio signal. In particular, the second audio feature may be less perceivable than the first audio feature.

FIG. 7 illustrates a block flow diagram for an exemplary method of processing input audio signal 511 indicative of a sound detected in the environment of the user to assist the user in engaging in a healthy living style. The method may be executed by processor 112 of hearing device 110 and/or processor 312 of communication device 310. At operation S11, input audio signal 511 provided by input transducer 115 is received. At operation S12, it is determined whether input audio signal 511 comprises an audio feature matching a sound pattern characteristic of sound emitted by a subject suitable to impact a physical and/or mental health of the user. At operation S13, when it is determined at S12 that input audio signal 511 comprises the audio feature, the audio feature is modified in the input audio signal so that an awareness of the user of a presence of the subject in the environment can be increased or decreased. At operation S14, the input audio signal is provided based on which output audio signal 512 can be outputted by output transducer 117. At operation S14 and/or before operation S13, an additional processing of input audio signal 511 may be performed, e.g., to amplify input audio signal 511 according to the needs of a hearing impaired user. When it is determined, at S12, that input audio signal 511 does not comprise the audio feature, the method proceeds with operation S14 such that operation S13 is omitted.

FIG. 8 illustrates a block flow diagram for another exemplary method of processing input audio signal 511 indicative of a sound detected in the environment of the user to assist the user in engaging in a healthy living style. At operation S21, user control data 521 is received. For instance, user control data 521 may be provided from a user interface, e.g., as illustrated in FIG. 5. The user interface may be implemented in hearing device 110 and/or in communication device 310 communicatively coupled to hearing device 110. At operation S22, it is determined whether user control data 521 is indicative of whether the user desires a modifying of the audio feature so as to increase or decrease, during the outputting of the audio signal, an awareness of the user of a presence of a subject suitable to impact his physical and/or mental health in the environment. If this is the case, at operation S22, the method illustrated in FIG. 7 is performed including operations S11, S12, S13, and S14.

Alternatively or additionally, at operation S22, it is determined whether user control data 521 is indicative of one or more said aspects of the physical and/or mental health of the user which the user desires to engage in, which may be selected by the user via the user interface, e.g., as illustrated in FIG. 5. At operation S22, the method illustrated in FIG. 7 is performed including operations S11, S12, S13, and S14, wherein operation S12 is performed depending on the one or more aspects of the physical and/or mental health indicated by user control data 521. In particular, sound pattern 523, 524, 525 employed in operation S12 may be selected depending on the one or more aspects of the physical and/or mental health indicated by user control data 521.

FIG. 9 illustrates a block flow diagram for another exemplary method of processing input audio signal 511 indicative of a sound detected in the environment of the user to assist the user in engaging in a healthy living style. At operation S31, sensor data 531 is received. Sensor data 531 may include any data provided from one or more of sensors 115, 131-139 included in sensor unit 120 and/or in sensor unit 320.

At operation S32, a parameter indicative of the physical and/or mental health of the user is monitored. The parameter indicative of the physical and/or mental health of the user may be related to one or more of the aspects of the physical and/or mental health of the user described above. For instance, sensor data provided by optical sensor 133 may be employed to determine a blood analyte level, e.g., an amount of water and/or glucose contained in the blood, which can be indicative of a drinking behavior of the user, e.g., dehydration, and/or an eating behavior of the user. Further, input audio signal 511 provided by input transducer 115 may be employed to determine a sound of gulping and/or swallowing and/or chewing by the user which can indicate the user drinking and/or eating.

As another example, input audio signal 511 provided by input transducer 115 may be monitored to determine a current mood of the user and/or an average mood over a predetermined time period. E.g., input audio signal 511 may contain an audio feature indicative of laughing and/or giggling of the user and/or of a voice of the user having a pitch indicative of a happy or unhappy mood and/or of crying and/or sobbing by the user and/or may contain keywords indicative of the user's mood. Further, sensor data provided by movement sensor 136 can be indicative of the user's mood. E.g., when the user is moving rather often and/or performing movement patterns such as dancing or running, a rather good mood of the user may be determined. When the user is not moving much over a longer time period and/or his body is shivering and/or his head is turned downwards, a rather unhappy mood of the user may be determined. Further, sensor data provided by any of physiological sensors 133, 134, 135 can be indicative of the user's mood. E.g., bioelectric sensor 134 may be implemented as an EEG sensor which can be employed for emotion detection (see, e.g., Gannouni S. et al., Sci Rep 11, 7071 (2021). https://doi.org/10.1038/s41598-021-86345-5) indicative of the user's mood. Further, properties of the user's blood may be monitored by optical sensor 133 and/or bioelectric sensor 134 implemented as an ECG sensor, e.g., a heart rate, blood pressure, blood oxygen saturation level (SpO$_2$), which may also indicate the user's mood. Further, the user's body temperature may be monitored by body temperature sensor 135 which may also give an indication of the user's mood.

As another example, input audio signal 511 provided by input transducer 115 may be monitored to determine a social activity of the user. E.g., input audio signal 511 may contain the voice of the user rather often and/or voices of other people speaking to the user indicating a rather high level of social activity of the user. Input audio signal 511 not containing people's voices over a longer time period may indicative a state of social isolation of the user. Further, sensor data provided by user interface 137 may indicate a social activity of the user. For instance, on the one hand, when the user is manipulating the user interface of communication device 410 for a long time period, it may be deduced that the user is performing a rather isolated activity, e.g., in front of a screen of a mobile phone, and not socially interacting with other people. On the other hand, when the user is employing the user interface of communication device 410 for social media services, it may be deduced that the user is socially connected to other people.

As another example, sensor data provided by movement sensor 115 may be monitored to determine a physical activity of the user. E.g., the user moving rather often and/or performing activities such as walking and/or running and/or cycling on a regular basis can indicate a high level of physical activity, and the user rarely moving can indicate a low level of physical activity. Further, sensor data provided by any of physiological sensors 133, 134, 135 can indicate a level of physical activity and/or body fitness, e.g., by monitoring a heart rate, blood pressure, blood oxygen saturation level (SpO$_2$), body temperature and/or the like.

As another example, input audio signal 511 provided by input transducer 115 may be monitored to determine a nervousness of the user. E.g., input audio signal 511 may contain the voice of the user having a pitch and/or tonality indicating a state of nervousness. Further, sensor data provided by bioelectric sensor 134 implemented as an EEG sensor, which can be employed for emotion detection, can also be indicative of the user being nervous.

As another example, sensor data provided by bioelectric sensor 134 implemented as an EEG sensor can be employed to track whether the user is sleeping or being awake and/or about a quality of the sleep of the user. Further, properties of the user's blood may be monitored by optical sensor 133 and/or bioelectric sensor 134 implemented as an ECG sensor and/or as an EOG sensor to determine whether the user is sleeping or awake. Further, input audio signal 511 provided by input transducer 115 may be monitored to determine a state of the user being awake or sleeping, e.g., based on a breathing pattern of the user.

As another example, sensor data provided by movement sensor 115 may be employed to determine whether the user is performing an activity related to his body hygiene. E.g., when the user is brushing his teeth, a corresponding pattern of the user moving his head and/or arm may be determined. Further, input audio signal 511 provided by input transducer 115 may be monitored to determine a sound of tooth brushing.

At operation S33, it is determined whether the parameter indicative of the physical and/or mental health of the user fulfills a condition. In particular, when the sensor data is indicative of one or more of said aspects of the physical and/or mental health of the user, the condition is determined to be fulfilled when the aspect of the physical and/or mental health of the user, as indicated by the parameter, is determined to be below a threshold. E.g., the aspect below the threshold may represent a critical value of dehydration and/or unhappiness and/or social isolation and/or body fitness and/or nervousness and/or lack of sleep and/or neglection of body hygiene.

At operation S34, when the parameter indicative of the physical and/or mental health of the user has been determined to fulfill the condition at S33, the method illustrated in FIG. 7 is performed including operations S11, S12, S13, and S14.

FIG. 10 illustrates a block flow diagram for another exemplary method of processing input audio signal 511 indicative of a sound detected in the environment of the user to assist the user in engaging in a healthy living style. At operation 541, context data 541 is received. Context data 541 comprises location data indicative of a current location of the user and/or time data indicative of a current time. E.g., context data 541 may be provided by location sensor 138 and/or clock 139 included in hearing device 110 and/or communication device 310. At S42, it is determined whether the context data fulfills a condition. In particular, the condition may be determined to be fulfilled when a current location of the user and/or current time, as indicated by the context data 541, matches a predetermined location and/or time. The engaging of the user in a healthy living style may thus be restricted to the predetermined location and/or time at which it can be beneficial or useful to the user. E.g., engaging the user in eating more may be particularly useful at dinner time and/or lunch time. Engaging the user to calm down before going to sleep may be particularly useful at bed time. At operation S43, when the context data has been determined to fulfill the condition at S42, the method illustrated in FIG. 7 is performed including operations S11, S12, S13, and S14.

While the principles of the disclosure have been described above in connection with specific devices, systems, and methods, it is to be clearly understood that this description is made only by way of example and not as limitation on the scope of the invention. The above described embodiments are intended to illustrate the principles of the invention, but not to limit the scope of the invention. Various other embodiments and modifications to those embodiments may be made by those skilled in the art without departing from the scope of the present invention that is solely defined by the claims. In the claims, the word "comprising" does not exclude other elements or steps, and the indefinite article "a" or "an" does not exclude a plurality. A single processor or controller or other unit may fulfil the functions of several items recited in the claims. The mere fact that certain measures are recited in mutually different dependent claims does not indicate that a combination of these measures cannot be used to advantage. Any reference signs in the claims should not be construed as limiting the scope.

The invention claimed is:

1. A method of operating a hearing device configured to be worn at an ear of a user to assist the user in engaging in a healthy living style, the method comprising:

receiving, from an input transducer included in the hearing device, an input audio signal indicative of a sound detected in an environment of the user;

processing the input audio signal;

outputting, by an output transducer included in the hearing device, an output audio signal based on the processed input audio signal so as to stimulate the user's hearing;

receiving sensor data including physiological data indicative of a physiological property of the user;

determining, based on the physiological data, whether the input audio signal comprises an audio feature matching a sound pattern characteristic of sound emitted by a subject suitable to impact at least one of a physical health or a mental health of the user; and, when the input audio signal comprises the audio feature, modifying, during the processing of the input audio signal, the audio feature in the input audio signal so as to increase or decrease, during the outputting of the output audio signal, an awareness of the user of a presence of the subject in the environment, wherein the physiological data is received from at least one of:

an optical sensor configured to emit light at a wavelength absorbable by an analyte contained in blood of the user;

a bioelectric sensor comprising at least one electrode configured to detect a bioelectric signal from the user's body; or a body temperature sensor configured to detect a temperature of the user's body.

2. The method of claim 1, wherein, during the determining whether the input audio signal comprises the audio feature, the input audio signal is input into a machine learning algorithm which at least one of separates the audio feature from the input audio signal or outputs a likelihood that the input audio signal comprises the audio feature, wherein the machine learning algorithm has been trained with previously recorded input audio signals characteristic of the sound emitted by the subject.

3. The method of claim 2, wherein, after the determining whether the input audio signal comprises the audio feature, the machine learning algorithm is trained with at least one of the input audio signal or the audio feature matching the sound pattern when it is determined that the input audio signal comprises the audio feature matching the sound pattern.

4. The method of claim 1, further comprising
receiving user control data indicative of whether the user desires said modifying of the audio feature, wherein at least one of the determining whether the input audio signal comprises the audio feature or the modifying of the audio feature in the input audio signal is performed depending on the user control data.

5. The method of claim 1, wherein the subject is of a type of subjects which are each suitable to impact an equal aspect of the at least one of the physical heath or the mental health of the user, wherein at least part of the subjects of the type emit a different sound and the sound pattern is characteristic of the different sound.

6. The method of claim 5, wherein an aspect of the at least one of the physical health or the mental health of the user includes at least one of:
at least one of a drinking or eating behavior of the user;
a mood of the user;
a social activity of the user;
a sleeping behavior of the user;
a nervousness and/or emotional stress of the user;
a physical activity of the user; and/or or
a tooth brushing behavior of the user.

7. The method of claim 5, further comprising
receiving user control data indicative of one or more aspects of the at least one of the physical heath or the mental health of the user which the user desires to engage in, wherein at least one of the determining whether the input audio signal comprises the audio feature or the modifying of the audio feature in the input audio signal is performed depending on the user control data.

8. The method of claim 1, wherein the
receiving of the sensor data further includes at least one of:
said input audio signal;
movement data indicative of a movement of the user; or
interaction data indicative of an interaction of the user with a user interface;
monitoring, based on the sensor data, a parameter indicative of the at least one of the physical health or the mental health of the user; and
determining whether the parameter fulfills a condition, wherein at least one of the determining whether the input audio signal comprises the audio feature or the modifying of the audio feature in the input audio signal is performed depending on the condition being fulfilled by the sensor data.

9. The method of claim 8, wherein the sensor data is indicative of one or more aspects of the at least one of the physical health or the mental health of the user and the condition is determined to be fulfilled when an aspect of the at least one of the physical health or the mental health of the user is determined to be below a threshold.

10. The method of claim 1, wherein the sound pattern is characteristic of at least one of:
a sound of opening a receptacle;
a sound of at least one of pouring, flowing, or splashing water;
a sound related to at least one of food preparation or food consumption;
a motor sound;
a sound typically occurring in at least one of a natural or rural environment;
a sound of a wild animal;
a sound of a domesticated animal;
a sound of a baby;
a sound of at least one of human laughter or giggling;
a sound of crackling fire;
a sound of blowing wind;
a sound of at least one of a music instrument or a singing voice;
a sound of a communication between humans;
a sound of a household appliance;
a sound of at least one of traffic noise or factory noise;
a voice of a significant other;
a sound of footsteps;
a sound related to people performing a physical activity; or
a sound of tooth brushing.

11. The method of claim 1, further comprising:
receiving context data including at least one of:
location data indicative of a current location of the user; or
time data indicative of a current time; and
determining whether the context data fulfills a condition, wherein at least one of the determining whether the input audio signal comprises the audio feature or the modifying of the audio feature in the input audio signal is performed depending on the condition being fulfilled by the context data.

12. The method according to claim 1, wherein said modifying the audio feature in the input audio signal comprises at least one of:
determining, based on the audio feature, a location of the subject associated with the sound pattern, and directing a beamformer toward the location;
increasing or decreasing a sharpness of the audio feature;
increasing or decreasing a volume of the audio feature;
altering a frequency of the audio feature;
suppressing the audio feature;
increasing a number of times in which the audio feature is included in the input audio signal;
extracting the audio feature from the input audio signal, altering a property of the audio feature, and adding the audio feature with the altered property to the input audio signal; or
superimposing, wherein said audio feature is a first audio feature, a second audio feature in the input audio signal.

13. A hearing device configured to be worn at an ear of a user, the hearing device comprising an input transducer, a processor, and an output transducer, wherein the processor is configured to perform the method according to claim 1.

14. A computer-readable medium storing instructions that, when executed by a processor included in a hearing device, cause the hearing device to perform operations of the method according to claim 1.

\* \* \* \* \*